(12) United States Patent
Kellett

(10) Patent No.: US 8,202,292 B2
(45) Date of Patent: Jun. 19, 2012

(54) VASO-OCCLUSIVE COIL DELIVERY SYSTEM

(75) Inventor: James B. Kellett, Los Gatos, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 442 days.

(21) Appl. No.: 12/575,048

(22) Filed: Oct. 7, 2009

(65) Prior Publication Data

US 2010/0094395 A1    Apr. 15, 2010

Related U.S. Application Data

(60) Provisional application No. 61/104,948, filed on Oct. 13, 2008.

(51) Int. Cl.
*A61M 29/00* (2006.01)
(52) U.S. Cl. ...................................................... 606/200
(58) Field of Classification Search .................. 623/1.11, 623/1.23, 2.11, 23.72; 606/200, 159; D24/143; 600/372, 373, 393; 604/104–107
See application file for complete search history.

(56) References Cited

U.S. PATENT DOCUMENTS

| | | | |
|---|---|---|---|
| 4,994,069 A | 2/1991 | Ritchart et al. | |
| 5,122,136 A | 6/1992 | Guglielmi et al. | |
| 5,226,911 A | 7/1993 | Chee et al. | |
| 5,304,194 A | 4/1994 | Chee et al. | |
| 5,382,259 A | 1/1995 | Phelps et al. | |
| 5,549,624 A | 8/1996 | Mirigian et al. | |
| 5,582,619 A | 12/1996 | Ken | |
| 5,690,666 A | 11/1997 | Berenstein et al. | |
| 5,743,905 A * | 4/1998 | Eder et al. | 606/32 |

(Continued)

FOREIGN PATENT DOCUMENTS

DE    10325130    9/2004

(Continued)

OTHER PUBLICATIONS

PCT International Search Report and Written Opinion for PCT/US2010/026831, Applicant Boston Scientific Scimed, Inc., Forms PCT/ISA/210, 220, and 237, dated Dec. 13, 2010 (16 pages).

(Continued)

*Primary Examiner* — Gary Jackson
*Assistant Examiner* — Christopher Schubert
(74) *Attorney, Agent, or Firm* — Vista IP Law Group LLP

(57) ABSTRACT

An occlusive coil delivery device includes an occlusive coil having a plurality of windings with the proximal end having a plurality of open pitched windings, and a delivery wire assembly having a proximal tubular portion and a distal coil portion with a lumen extending at least partially through the assembly, the assembly including a delivery wire forming a first conductive path extends through the lumen from a proximal end of the delivery wire assembly to a location distal with respect to the distal coil portion, the distal extension including a sacrificial detachment zone. The delivery wire assembly further includes a second conductive path formed by the proximal tubular portion and distal coil portion, with the delivery device further including a delivery wire adapter having a proximal end and a distal end, the distal end of the adapter comprising a plurality of fingers configured to interface between adjacent open pitched windings of the proximal end of the occlusive coil, with the proximal end of the delivery wire adapter secured to a distal portion of the delivery wire.

12 Claims, 9 Drawing Sheets

U.S. PATENT DOCUMENTS

| | | | |
|---|---|---|---|
| 5,853,418 A | 12/1998 | Ken et al. | |
| 5,919,187 A | 7/1999 | Guglielmi et al. | |
| 5,984,929 A | 11/1999 | Bashiri et al. | |
| 6,077,260 A | 6/2000 | Wheelock et al. | |
| 6,102,933 A * | 8/2000 | Lee et al. | 606/209 |
| 6,277,125 B1 * | 8/2001 | Barry et al. | 606/108 |
| 6,280,457 B1 | 8/2001 | Wallace et al. | |
| 6,409,721 B1 | 6/2002 | Wheelock et al. | |
| 6,468,266 B1 * | 10/2002 | Bashiri et al. | 606/1 |
| 6,537,293 B1 * | 3/2003 | Berryman et al. | 606/200 |
| 6,575,965 B1 * | 6/2003 | Fitch et al. | 606/15 |
| 6,589,230 B2 | 7/2003 | Gia et al. | |
| 6,953,473 B2 * | 10/2005 | Porter | 606/213 |
| 7,198,613 B2 | 4/2007 | Gandhi et al. | |
| 7,862,602 B2 * | 1/2011 | Licata et al. | 623/1.11 |
| 7,921,848 B2 * | 4/2011 | Nikolchev et al. | 128/830 |
| 2002/0151883 A1 | 10/2002 | Guglielmi | |
| 2003/0120300 A1 * | 6/2003 | Porter | 606/191 |
| 2003/0130689 A1 * | 7/2003 | Wallace et al. | 606/200 |
| 2004/0002732 A1 | 1/2004 | Teoh et al. | |
| 2004/0002733 A1 | 1/2004 | Teoh | |
| 2004/0010243 A1 | 1/2004 | Klint | |
| 2006/0135986 A1 | 6/2006 | Wallace et al. | |
| 2006/0271097 A1 | 11/2006 | Ramzipoor et al. | |
| 2006/0282112 A1 | 12/2006 | Griffin | |
| 2007/0055302 A1 * | 3/2007 | Henry et al. | 606/200 |
| 2007/0123927 A1 * | 5/2007 | Farnan | 606/200 |
| 2009/0018653 A1 * | 1/2009 | Bashiri et al. | 623/11.11 |
| 2009/0062726 A1 * | 3/2009 | Ford et al. | 604/57 |
| 2009/0177261 A1 * | 7/2009 | Teoh et al. | 623/1.11 |
| 2009/0299275 A1 * | 12/2009 | Gandhi et al. | 604/57 |
| 2010/0094395 A1 * | 4/2010 | Kellett | 623/1.11 |
| 2011/0160835 A1 * | 6/2011 | Licata et al. | 623/1.11 |

FOREIGN PATENT DOCUMENTS

| | | |
|---|---|---|
| WO | 9942038 | 8/1999 |
| WO | 03053281 | 7/2003 |
| WO | 2008064206 | 5/2008 |
| WO | 2008085606 | 7/2008 |
| WO | 2008/144587 | 11/2008 |
| WO | WO 2008144587 A2 * | 11/2008 |

OTHER PUBLICATIONS

PCT Invitation to Pay Additional Fees from the International Search Authority for PCT/US2010/026831, Applicant Boston Scientific Scimed, Inc., Form PCT/ISA/206 and Annex to Form PCT/ISA/206, dated Jul. 23, 2010 (5 pages).

Non final Office Action dated Nov. 12, 2010, for related U.S. Appl. No. 12/122,636, filed May 16, 2008, Inventor Russell Ford et al. (29 pages).

PCT International Search Report and the Written Opinion for PCT/US2010/029700, Applicant Boston Scientific Scimed, Inc., Forms PCT/ISA 210, 220, and 237, dated May 21, 2010 (12 pages).

PCT International Search Report and Written Opinion for PCT/US2009/059797, Applicant Boston Scientific Scimed, Inc., Forms PCT/ISA/210, 220, and 237 dated Nov. 30, 2009 (14 pages).

PCT International Search Report and Written Opinion for PCT/US2008/064013, Applicant Boston Scientific Scimed, Inc., Forms PCT/ISA/210, 220, and 237 dated May 16, 2009 (16 pages).

PCT Invitation to Pay Additional Fees from the International Search Authority for PCT/US2008/064013, Applicant Boston Scientific Scimed, Inc., Form PCT/ISA/206 and Annex to Form PCT/ISA/206, dated Jan. 29, 2009 (5 pages).

* cited by examiner

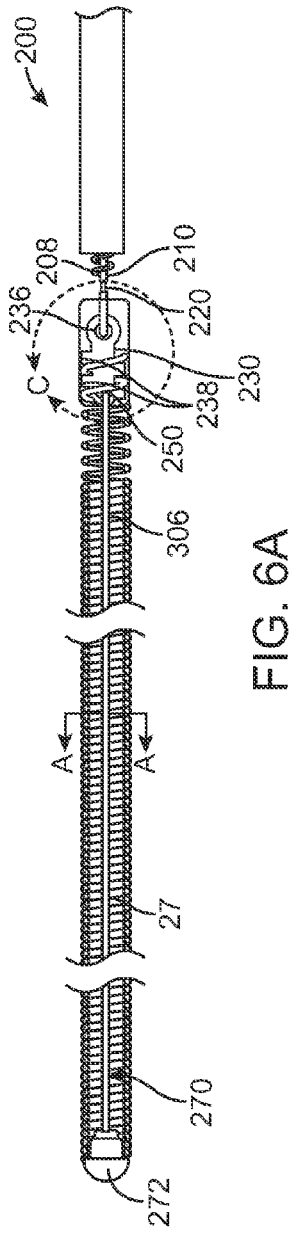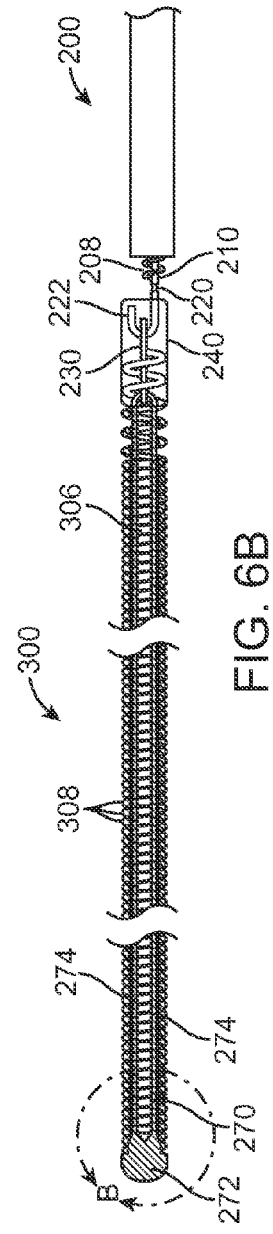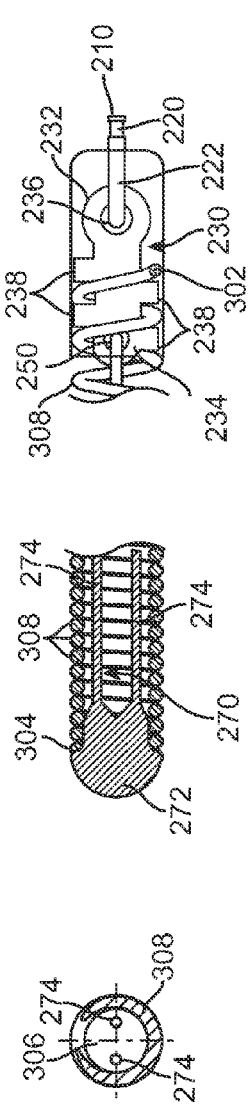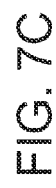

VASO-OCCLUSIVE COIL DELIVERY SYSTEM

RELATED APPLICATION DATA

The present application claims the benefit under 35 U.S.C. §119 to U.S. provisional patent application Ser. No. 61/104,948, filed Oct. 13, 2008. The foregoing provisional application is hereby incorporated by reference into the present application in its entirety.

FIELD OF INVENTION

The field of invention generally relates to systems and delivery devices for implanting vaso-occlusive devices for establishing an embolus or vascular occlusion in a vessel of a human or veterinary patient.

BACKGROUND

Vaso-occlusive devices or implants are used for a wide variety of reasons, including treatment of intra-vascular aneurysms. A common vaso-occlusive device takes the form of a soft, helically wound coil formed by winding a platinum (or platinum alloy) wire strand about a primary mandrel. The relative stiffness of the coil will depend, among other things, on its composition, the diameter of the wire strand, the diameter of the primary mandrel, and the pitch of the primary windings. The coil is then wrapped around a larger, secondary mandrel, and heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site, e.g., an aneurysm, in the vasculature, it is well-known to first position a small profile, delivery catheter or micro-catheter at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the pusher wire is extended out of the distal end opening of the micro-catheter and into the aneurysm. The vaso-occlusive device is then released or "detached" from the end pusher wire, and the pusher wire is withdrawn back through the catheter. Depending on the particular needs of the patient, another occlusive device may then be pushed through the catheter and released at the same site.

One known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

One perceived problem with current embolic detachment schemes is that the junction between the delivery wire and the occlusive member (e.g., coil) can be relatively long and stiff. For example, various intermediate coils and PET bonding joints between the distal end of the delivery wire and the occlusive coil add stiffness to the overall structure. A stiff junction between the delivery wire and the occlusive member complicates accurate placement of the delivery system at the desired location. For example, a stiff section of the delivery wire or the delivery wire/coil junction can cause a pre-shaped micro-catheter to kick back or recoil from the aneurysm upon coil release.

Another perceived problem with some current embolic detachment devices is that a separate return or ground electrode is used to complete the electrical circuit between the external power supply and the electrolytically detachable coil. This separate return or ground electrode may be a patch that is placed on the patient's body or a needle that is inserted into the patient's groin area. The use of a separate, return or ground electrode does, however, introduce variability into the detachment time(s) of the occlusive coils. Variability is produced because of different tissue types and densities that exist between the occlusive device and the return electrode. Also, for grounding needles that are placed in the groin area of the patient, some patients experience discomfort or pain.

There thus is a need for a vaso-occlusive delivery system that reduces the overall length and stiffness of the junction between the delivery wire and the occlusive coil. Such a system should be easy to use yet provide for consistent detachment of embolic elements in the desired location. Moreover, the delivery system should be able to release the embolic element without extensive movement or kick-back motion resulting from the detachment operation. There is also a need for a vaso-occlusive delivery system that reduces variability in detachment times for occlusive devices. In this regard, there also is a need for alternative return or ground electrode configurations that do not utilize a separate, external return electrode such as a patch or grounding needle.

SUMMARY

In one embodiment, an occlusive coil delivery system includes an occlusive coil comprising a plurality of windings, the occlusive coil having a proximal end and a distal end, the proximal end of the occlusive coil comprising a plurality of open pitched windings. The system further includes a delivery wire adapter having a proximal end and a distal end, the distal end of the adapter comprising a plurality of fingers configured to interface between adjacent open pitched windings of the proximal end of the occlusive coil. The system also includes a delivery wire secured to the proximal end of the delivery wire adapter, the delivery wire comprising a sacrificial detachment region in a portion thereof. The sacrificial detachment region may break or otherwise dissolve in response to electrical energy (e.g., electrolytic detachment region) or thermal energy (e.g., thermal detachment region).

According to yet another embodiment, a method is disclosed for securing a delivery wire to an occlusive coil using a delivery wire adapter having a proximal end and a distal end, the distal end of the delivery wire adapter comprising a plurality of fingers configured to interface between adjacent open pitched windings of the proximal end of the occlusive coil. The method includes forming open pitched windings in a proximal end of the occlusive coil and rotating at least one of the occlusive coils and the delivery wire adapter about the plurality of fingers to form an interface between the occlusive coil and the delivery wire adapter. The interface between the occlusive coil and the delivery wire adapter may be made secure through the use of an adhesive such as an epoxy. The delivery wire is then secured to a proximal end of the delivery wire adapter.

According to another embodiment, an occlusive coil delivery device includes an occlusive coil having a plurality of windings with the proximal end having a plurality of open pitched windings. The delivery device also includes a delivery wire assembly having a proximal tubular portion and a distal coil portion and lumen extending at least partially therethrough. A delivery wire forming a first conductive path extends through the lumen from a proximal end of the delivery wire assembly to a location distal with respect to the distal coil portion. The distal extension includes an electrolytic detachment zone. The delivery wire assembly further includes a second conductive path formed by the proximal tubular portion and distal coil portion. The delivery device further includes a delivery wire adapter having a proximal end and a distal end, the distal end of the adapter comprising a plurality of fingers configured to interface between adjacent open pitched windings of the proximal end of the occlusive coil. The proximal end of the delivery wire adapter is secured to a distal portion of the delivery wire.

In still another aspect of the invention, a system for delivering an occlusive coil includes a delivery catheter having a proximal end and a distal end and a lumen extending between the proximal and distal ends. The delivery catheter may include, for example, a microcatheter. The system includes a delivery wire assembly having a proximal end and a distal end, the delivery wire assembly including a proximal tubular portion and a distal coil portion. A delivery wire formed as part of the delivery wire assembly forms a first conductive path and extends from the proximal end of the delivery wire assembly to a location distal with respect to the distal coil portion, the portion extending distally with respect to the distal coil portion having an electrolytic detachment zone. The delivery wire assembly further includes a second conductive path formed by the proximal tubular portion and distal coil portion. The second conductive path is electrically isolated from the first conductive path.

The system includes an occlusive coil comprising a plurality of windings, the occlusive coil having a proximal end and a distal end, the proximal end of the occlusive coil comprising a plurality of open pitched windings. The system also has a delivery wire adapter having a proximal end and a distal end, the distal end of the delivery wire adapter comprising a plurality of fingers configured to interface between adjacent open pitched windings of the proximal end of the occlusive coil. The proximal end of the delivery wire adapter is configured for attachment to a distal portion of the delivery wire. The system includes a power supply configured to electrically connect to the first conductive path and the second conductive path. The power supply delivers current to the delivery wire and the electrolytic sacrificial link contained therein which electrolytically dissolves in the presence of bodily fluids (or flushing solutions).

BRIEF DESCRIPTION OF THE DRAWINGS

As seen in FIG. 4 a delivery wire secured to a proximal end of the delivery wire adapter of the type illustrated in FIG. 2. The distal end of the delivery wire adapter is secured to a proximal end of the occlusive coil. In this embodiment, an outer retaining sleeve is disposed about the periphery of a portion of the occlusive coil.

FIG. 6A illustrates a cross-sectional view of the interface between the distal end of the delivery wire assembly and the occlusive coil according to one embodiment.

FIG. 6B illustrates an orthogonal cross-sectional view (with respect to FIG. 6A) of the interface between the distal end of the delivery wire assembly and the occlusive coil.

FIG. 7A illustrates a cross-sectional view of the occlusive coil taken along the line A-A in FIG. 6A.

FIG. 7B illustrates a detailed view of the region B illustrated in FIG. 6B.

FIG. 7C illustrates a detailed view of the region C illustrated in FIG. 6A.

DETAILED DESCRIPTION OF THE ILLUSTRATED EMBODIMENTS

Figure 1:
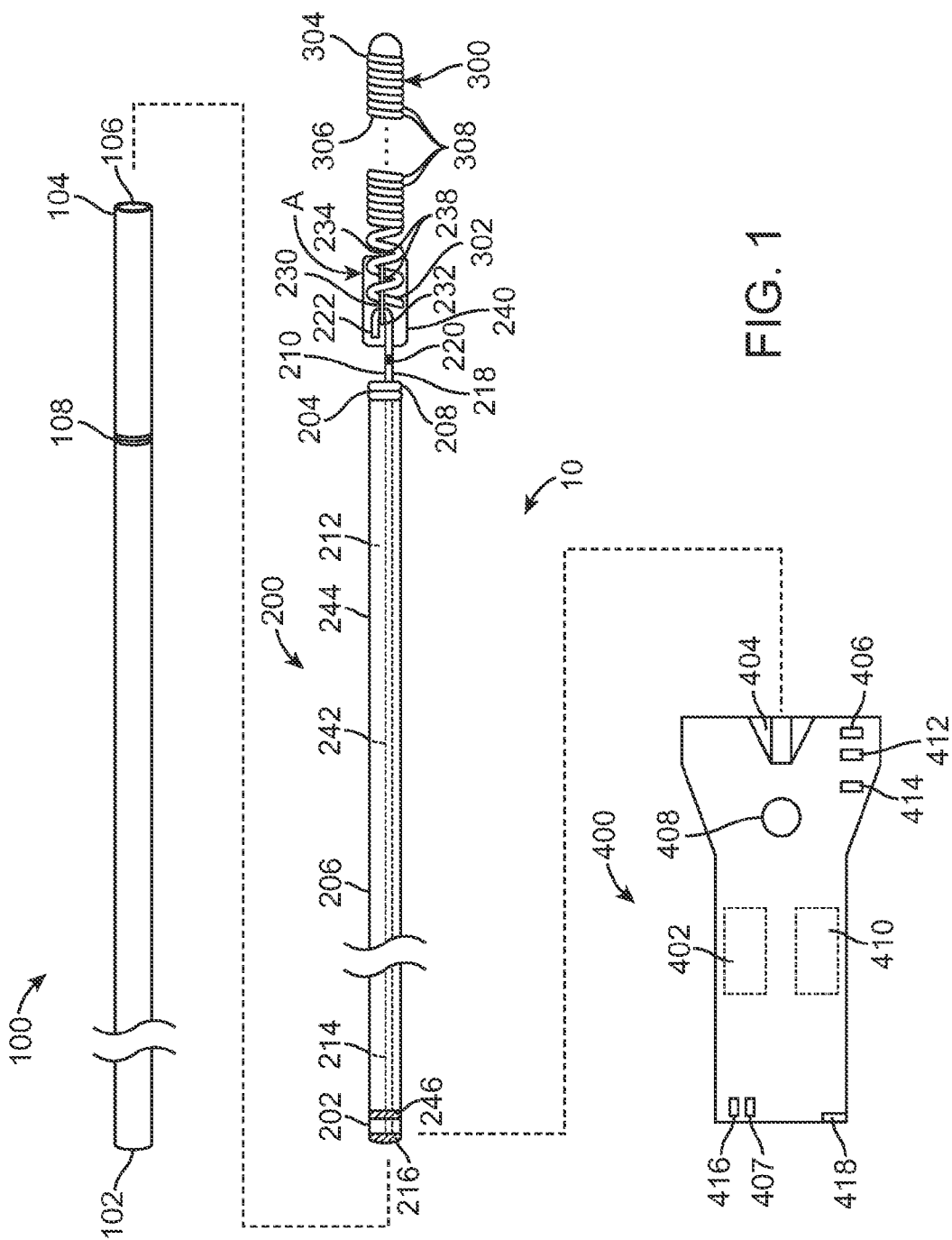
FIG. 1 illustrates an occlusive coil delivery system according to one embodiment.

FIG. 1 illustrates an occlusive coil delivery system 10 according to one embodiment. The system 10 includes a number of subcomponents or sub-systems. These include a delivery catheter 100, a delivery wire assembly 200, an occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the delivery wire assembly 200. Further, the lumen 106 is sized for the passage of a guidewire (not shown) which may optionally be used to properly guide the delivery catheter 100 to the appropriate delivery site. The delivery catheter 100 may include a braided-shaft construction of stainless steel flat wire that is encapsulated or surrounded by a polymer coating. For example, HYDROLENE® is one exemplary polymer coating that may be used to cover the exterior portion of the delivery catheter 100. Of course, the system 10 is not limited to a particular construction or type of delivery catheter 100 and other constructions known to those skilled in the art may be used for the delivery catheter 100.

The inner lumen 106 is advantageously coated with a lubricious coating such as PTFE to reduce frictional forces between the delivery catheter 100 and the device that is being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 106 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the delivery wire assembly 200 and occlusive coil 300 but generally the diameter lumen 106 of the delivery catheter 100 (I.D. of delivery catheter 100) is less than about 0.02 inches. In some embodiments, the delivery catheter 100 may be known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Still referring to FIG. 1, the system 10 includes a delivery wire assembly 200 that is configured for axial movement within the lumen 106 of the delivery catheter 100. The delivery wire assembly 200 generally includes a proximal end 202 and a distal end 204. In one embodiment, the delivery wire assembly 200 includes a proximal tubular portion 206 and a distal coil portion 208. The proximal tubular portion 206 may be formed from, for example, stainless steel hypotube. As explained in further detail herein, the distal coil portion 208 may be bonded to the proximal tubular portion 206 in an end-to-end arrangement. The delivery wire assembly 200 further includes a delivery wire 210 that extends from the proximal end 202 of the delivery wire assembly 200 to a location that is distal with respect to the distal end 204 of the delivery wire assembly 200. The delivery wire 210 is disposed within a lumen 212 that extends within an interior portion of the delivery wire assembly 200.

The delivery wire 210 is formed from an electrically conductive material such as stainless steel wire. The proximal end 214 of the delivery wire 210 (shown in phantom) is electrically coupled to an electrical contact 216 located at the proximal end 202 of the delivery wire assembly 200. The electrical contact 216 may be formed from a metallic solder (e.g., gold) that is configured to interface with a corresponding electrical contact (not shown) in the power supply 400. A portion of the delivery wire 210 is advantageously coated with an insulative coating 218. The insulative coating 218 may include polyimide. In one embodiment, the entire length of the delivery wire 210 is coated with an insulative coating 218 except for a small region 220 located in portion of the delivery wire 210 that extends distally with respect to the distal end 204 of the of the delivery wire assembly 200. This "bare" portion of the delivery wire 210 forms the electrolytic detachment zone 220 which dissolves upon application of electrical current from the power supply 400.

In an alternative embodiment, instead of an electrolytic detachment zone 220, the sacrificial region may be configured to break or dissolve in response to thermal energy. For example, the detachment zone 220 may be formed from a polymeric link (e.g., fiber(s)) that melts or dissolves in response to externally applied thermal energy or heat. The polymeric link may be formed from a thermoplastic material (e.g., polyethylene) that has a high tensile strength and appropriate melting temperature. The thermally responsive sacrificial region may be responsive to an electrical resistance heater coil that is configured to apply to the detachment zone 220. Such heater coils operate by generating heat in response to an applied electrical current. Alternatively, electromagnetic or RF energy may be used to break or dissolve the sacrificial region. U.S. Pat. No. 7,198,613, which is incorporated herein by reference, discloses additional details regarding various thermally-actuated detachment modalities.

Still referring to FIG. 1, the distal end 222 of the delivery wire 210 terminates in a hook or "J" shape. An occlusive coil 300 is shown in FIG. 1 as being secured to the distal end 222 of the delivery wire 210 via a delivery wire adapter 230. The delivery wire adapter 230 includes a proximal end 232 and a distal end 234. The proximal end 232 of the delivery wire adapter 230 includes an aperture 236 (seen in FIG. 2) that is dimensioned to receive the distal end 222 of the delivery wire 210. In this regard, the hook portion of the delivery wire 210 passes through the aperture 236 to secure the delivery wire 210 to the proximal end 232 of the delivery wire adapter 230. The middle and distal end 234 of the delivery wire adapter 230 includes a plurality of fingers 238 or lugs (best seen in FIG. 2). The fingers 238 disposed on the delivery wire adapter 230 are configured to interface with the occlusive coil 300.

In particular, the occlusive coil 300 includes a proximal end 302, a distal end 304 and a lumen 306 extending therebetween. The occlusive coil 300 is generally made from a biocompatible metal such as platinum or a platinum alloy (e.g., platinum-tungsten alloy). The occlusive coil 300 generally includes a straight configuration (as illustrated in FIG. 1) when the occlusive coil 300 is loaded within the delivery catheter 100. Upon release, the occlusive coil 300 generally takes a secondary shape which may include two-dimensional or three-dimensional configurations such as that illustrated in FIG. 8. Of course, the system 10 described herein may be used with occlusive coils 300 having a variety of configurations and is not limited to particular occlusive coils 300 having a certain size or configuration.

The occlusive coil 300 includes a plurality of coil windings 308. The coil windings 308 are generally helical about a central axis disposed along the lumen 306 of the occlusive coil 300. As seen in FIG. 1, the proximal end 302 of the occlusive coil 300 has coil windings 308 with an open pitch configuration. For example, several of the proximal coil windings 308 may be spread open in the open pitch configuration (illustrated by arrow A in FIG. 1). The remaining distal portion of the occlusive coil 300 may have a closed pitch configuration as illustrated in FIG. 1. Of course, the distal portion of the occlusive coil 300 may also include one or more open pitch segments or regions (or the entire occlusive coil 300 may be open pitched). The open pitch of the proximal coil windings 308 provides a threaded-like recess for the interface fit with the corresponding fingers 238 of the delivery wire adapter 230.

While the fingers 238 of the delivery wire adapter 230 does secure the occlusive coil 300 to the delivery wire adapter 230, it is preferable to apply an adhesive 240 to the interface between the delivery wire adapter 230 and the proximal coil windings 308 of the occlusive coil 300. The adhesive 240 may also cover the junction formed between the distal end 222 of the delivery wire 210 and the proximal end 232 of the delivery wire adapter 230. The adhesive 240 may include an epoxy material which is cured or hardened through the application of heat or UV radiation. For example, the adhesive 240 may include a thermally cured, two-part epoxy such as EPO-TEK® 353ND-4 available from Epoxy Technology, Inc., 14 Fortune Drive, Billerica, Mass. The adhesive 240 encapsulates and locates the delivery wire adapter 230 substantially concentrically relative to the occlusive coil 300 and prevents tangential motion that may be induced by axially tensile loading of the occlusive coil 300.

As an alternative to the use of an adhesive 240, adjacent coil windings 308 on either side of the fingers 238 may be joined by laser tack, spot, or continuous welding. Alternatively, laser melting of the fingers 238 over the coil windings 308 may be used to mechanically join the delivery wire adapter 230 to the occlusive coil 300.

Figure 5:
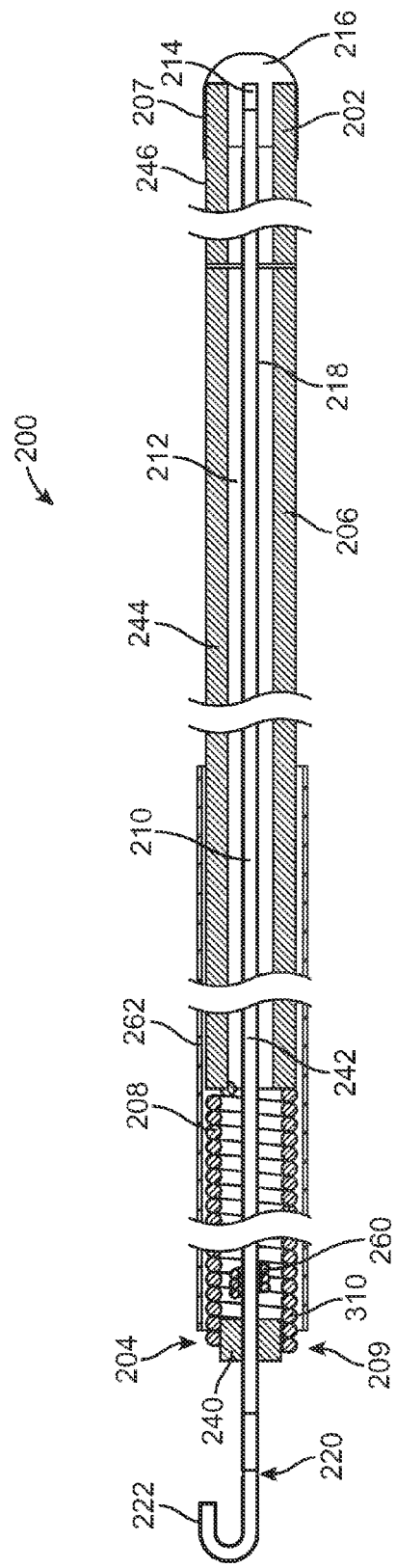
FIG. 5 illustrates a cross-sectional view of a delivery wire assembly according to one embodiment.

Still referring to FIG. 1, the proximal tubular portion 206 and a distal coil portion 208 form a return electrode for the delivery system 10. In this regard, the delivery wire 210 forms a first conductive path 242 between the electrical contact 216 and the electrolytic detachment zone 220. This first conductive path 242 may comprise the anode (+) of the electrolytic circuit when the delivery wire assembly 200 is operatively coupled to the power supply 400. A second conductive path 244 is formed by the proximal tubular portion 206 and a distal coil portion 208 of the delivery wire assembly 200. The second conductive path 244 is electrically isolated from the first conductive path 242. The second conductive path 244 may comprise the cathode (−) or ground electrode for the electrical circuit. An electrical contact 246 for the second conductive path 244 may be disposed on a proximal end of the tubular portion 206. In one embodiment, the electrical contact 246 is simply an exposed portion of the tubular portion 206 since the tubular portion 206 is part of the second conductive path 244. For instance, a proximal portion of the tubular portion 206 that is adjacent to the electrical contact 216 may be covered with an insulative coating 207 such as polyimide as illustrated in FIG. 5. An exposed region of the tubular portion 206 that does not have the insulative coating may form the electrical contact 246. Alternatively, the electrical contact 246 may be a ring type electrode or other contact that is formed on the exterior of the tubular portion 206.

The electrical contact 246 is configured to interface with a corresponding electrical contact (not shown) in the power supply 400 when the proximal end 202 of the delivery wire assembly 200 is inserted into the power supply 400. The electrical contact 246 of the second conductive path 244 is, of course, electrically isolated with respect to the electrical contact 216 of the first conductive path 242.

Still referring to FIG. 1, the system 10 includes a power supply 400 for supplying direct current to the delivery wire 210 which contains the electrolytic detachment zone 220. In the presence of an electrically conductive fluid (which may include a physiological fluid such as blood or a flushing solution such as saline), when the power supply 400 is activated, electrical current flows in a circuit within the first conductive path 242 and the second conductive path 244. After several seconds (generally less than about 10 seconds), the sacrificial electrolytic detachment zone 220 dissolves and the occlusive coil 300 separates form the delivery wire 210.

The power supply 400 will include an onboard energy source such as batteries (e.g., 2 AAA batteries) along with drive circuitry 402. The drive circuitry 402 may include one or more microcontrollers or processors configured to output a driving current. The power supply 400 illustrated in FIG. 1 includes a receptacle 404 that is configured to receive and mate with the proximal end 202 of the delivery wire assembly 200. Upon insertion of the proximal end 202 into the receptacle 404, the electrical contacts 216, 246 disposed on the delivery wire assembly 200 electrically couple with corresponding contacts (not shown) located in the power supply 400. A visual indicator 406 (e.g., LED light) may indicate when the proximal end 202 of delivery wire assembly 200 has been properly inserted into the power supply 400. Another visual indicator 407 may activate if the batteries need to be replaced. The power supply 400 typically includes an activation trigger or button 408 that is depressed by the user to apply the electrical current to the sacrificial electrolytic detachment zone 220. Typically, once the activation trigger 408 has been activated, the driver circuitry 402 automatically supplies current until detachment occurs. The drive circuitry 402 typically operates by applying a substantially constant current (e.g., around 1.5 mA).

The power supply 400 may include optional detection circuitry 410 that is configured to detect when the occlusive coil 300 has detached from the delivery wire 210. The detection circuitry 410 may identify detachment based upon a measured impedance value. A visual indicator 412 may indicate when the power supply 400 is being supplied to the current to the sacrificial electrolytic detachment zone 220. Another visual indicator 414 may indicate when the occlusive coil 300 has detached from the delivery wire 210. As an alternative to the visual indicator 414, an audible signal (e.g., beep) or even tactile signal (e.g., vibration or buzzer) may be triggered upon detachment. The detection circuitry 410 may be configured to disable the drive circuitry 402 upon sensing detachment of the occlusive coil 300.

The power supply 400 may also contain another visual indicator 416 that indicates to the operator when a legacy, non-bipolar delivery wire assembly is inserted into the power supply 400. As explained in the background above, prior devices used a separate return electrode that typically was in the form of a needle that was inserted into the groin area of the patient. The power supply 400 is configured to detect when one of the older non-bipolar delivery wire assemblies has been inserted. Under such situations, the visual indicator 416 (e.g., LED) is turned on and the user is advised to insert the separate return electrode (not shown in FIG. 1) into a port 418 located on the power supply 400.

Figure 2:
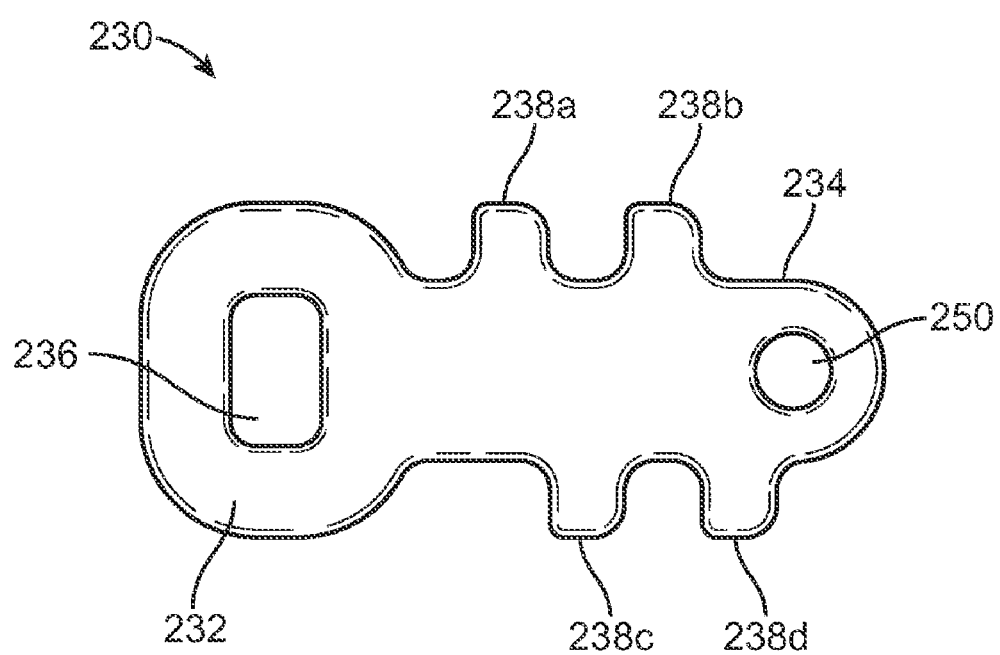
FIG. 2 is a plan view of a delivery wire adapter according to one embodiment.

FIG. 2 illustrates an enlarged, side view of a delivery wire adapter 230 according to one embodiment. FIG. 2 illustrates the aperture 236 located in the proximal end 232 of the delivery wire adapter 230. FIG. 2 also illustrates an optional aperture 250 formed in the distal end 234 of the delivery wire adapter 230. The optional aperture 250 may be used to secure the distal end 234 of the delivery wire adapter 230 to a stretch resistant member as described in more detail below. Of course, the aperture 250 is entirely optional and may be omitted in certain embodiments. The apertures 236, 250 may be made smooth by application of a small drop of adhesive. Alternatively, the inner surface of the apertures 236, 250 may be chamfered by electrical discharge machining (EDM).

FIG. 2 further illustrates four (4) separate fingers 238a, 238b, 238c, 238d located on the delivery wire adapter 230 with two (2) such fingers 238a, 238b disposed on one side and two other fingers 238c, 238d located on the opposing side of the delivery wire adapter 230. Other embodiments may include different numbers of fingers 238 on the delivery wire adapter 230 so long as there is at least one finger 238 disposed on a first side of the delivery wire adapter 230 and at least one second finger 238 disposed on a second, opposing side of the delivery wire adapter 230. For example, one alternative embodiment uses a delivery wire adapter 230 with two fingers 238a, 238b on one side with only a single finger (either 238c or 238d) disposed on a second, opposing side. This configuration of the delivery wire adapter 230 is illustrated, for example, in FIG. 9B (prior to excess material being trimmed).

The delivery wire adapter 230 may be formed from a biocompatible metallic material such as hardened stainless steel 304 alloy. Of course, other metallic materials may also be used. As explained in more detail with respect to FIGS. 9A and 9B, multiple delivery wire adapters 230 may be formed from a single sheet or substrate.

The completed delivery wire adapter 230 such as that illustrated in FIG. 2 may have a length of less than 0.03 inches. For example, in one embodiment, the delivery wire adapter 230 may have a length within the range of about 0.02 inches to about 0.03 inches. The thickness of the delivery wire adapter 230 is a function of the thickness of the sheet or substrate from which it is made but generally is less than 0.003 inches. Of course, dimensions other than those expressly mentioned above are contemplated to fall within the scope of the invention.

Figure 3:
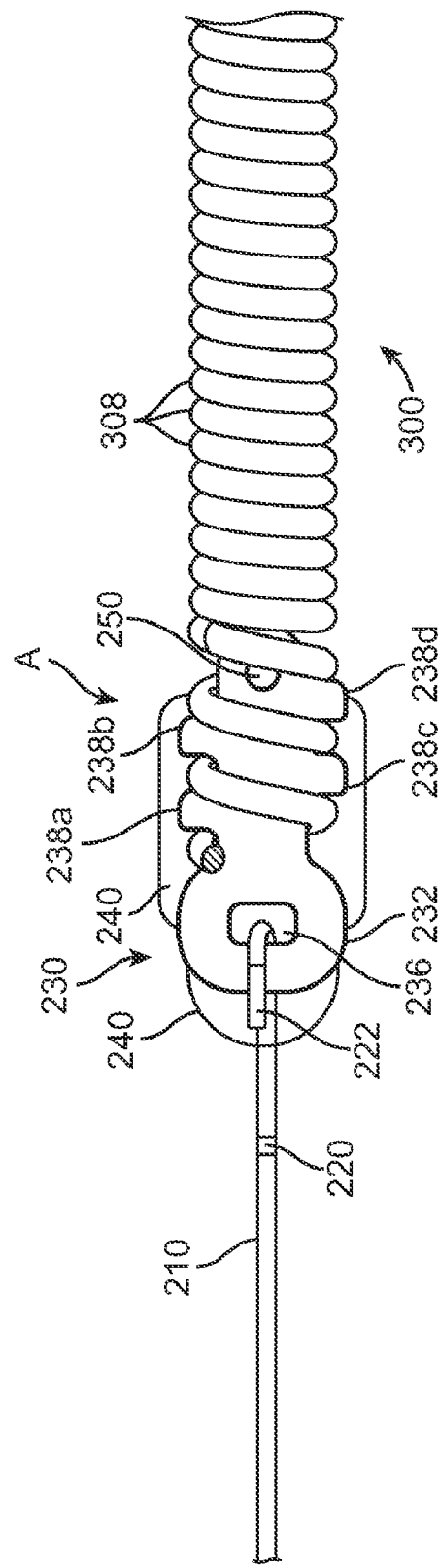
FIG. 3 illustrates a delivery wire secured to a proximal end of the delivery wire adapter of the type illustrated in FIG. 2. The distal end of the delivery wire adapter is secured to a proximal end of the occlusive coil.

FIG. 3 illustrates the interface formed between the delivery wire adapter 230 and the proximal end 302 of the occlusive coil 300. As seen in FIG. 3, the fingers 238a, 238b, 238c, 238d of the delivery wire adapter 230 are located between adjacent coil windings 308 of the open pitched region A. To load the delivery wire adapter 230 onto the proximal end 302 of the occlusive coil 300, several coil windings 308 of the proximal end 302 (e.g., 2-3 windings) are pulled axially to cause them to open into the open pitch configuration illustrated in FIG. 3. Either or both the delivery wire adapter 230 and occlusive coil are rotated about the fingers 238a, 238b, 238c, 238d until the delivery wire adapter 230 advances to the loaded configuration illustrated in FIG. 3. In this regard, the fingers 238a, 238b, 238c, 238d are interlaced between adjacent open-pitched windings 208. Adhesive 240 may be placed over the interface between the fingers 238a, 238b, 238c, 238d and the coil windings 308 to form a tight, secure bond between the two components. FIG. 3 also illustrates a bead of adhesive 240 covering the distal end 222 of the delivery wire 210 and the proximal end 232 of the delivery wire adapter 230. The adhesive bead 240 may be separate from the adhesive 240 applied over the coil windings 308 or, alternatively, or the two may combine into one joint as illustrated in FIG. 1.

Figure 4:
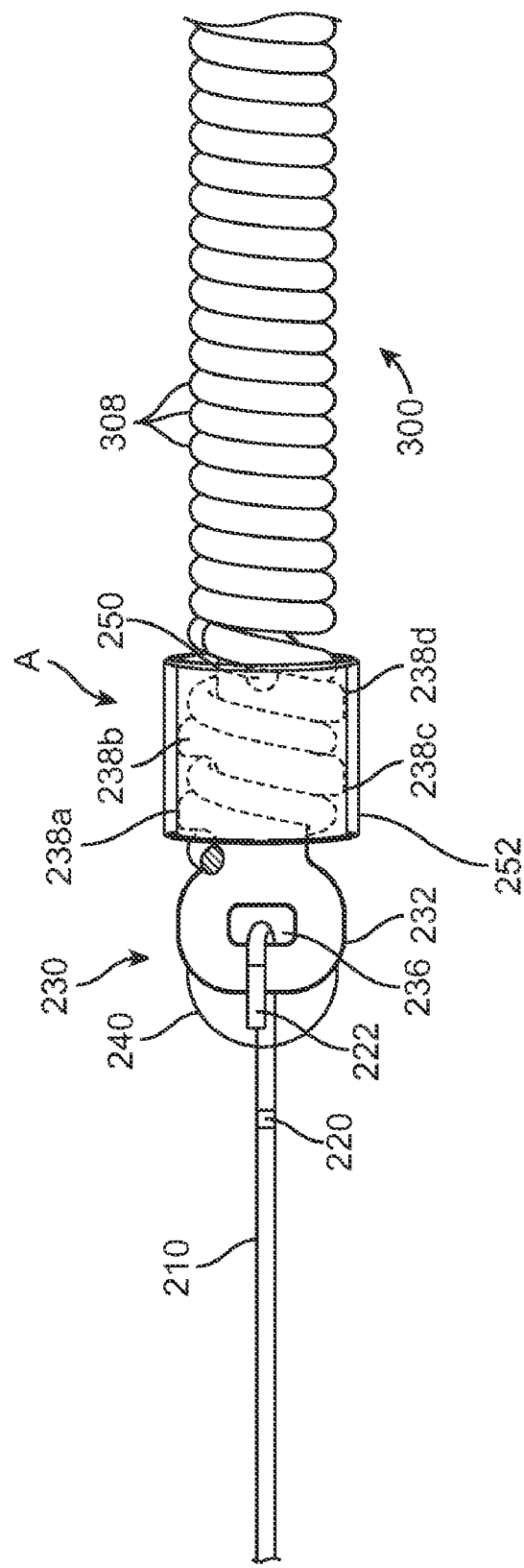
FIG. 4 illustrates an alternative embodiment.

FIG. 4 illustrates an alternative embodiment in which an optional external sleeve 252 is disposed about the periphery of the coil windings 308 in the region A having the open pitch. The external sleeve 252 acts as a containment sleeve to prevent dislodgement of the occlusive coil 300 from the delivery wire adapter 230. The sleeve 252 may be made from a metallic material or even a polymer if sufficiently strong. The sleeve 252 prevents radial displacement of the coil windings 308 when the junction is axially loaded.

FIG. 5 illustrates a cross-sectional view of the delivery wire assembly 200 according to one embodiment. Similar elements of this embodiment are identified with the same reference numbers as discussed above with respect to FIGS. 1-4. The delivery wire assembly 200 includes a proximal end 202 and a distal end 204 and measures between around 183 cm to around 187 cm in length. The delivery wire assembly 200 includes a proximal tubular portion 206 and a distal coil portion 208. The proximal tubular portion 206 may be formed from 304 stainless steel hypotube having an OD of 0.0125 inches and ID of 0.00825 inches. The length of the hypotube section may be between around 140 cm to around 150 cm, although other lengths may also be used.

As seen in FIG. 5, a distal coil portion 208 is bonded in end-to-end fashion to the distal face of the proximal tubular portion 206. The bonding may be accomplished using a weld or other bond. The distal coil portion 208 may have a length of around 39 cm to around 41 cm in length. The distal coil portion 208 may comprise a coil of 0.0025 inches×0.006 inches. This dimension generally refers to the internal mandrel used to wind the coil wire around to form the plurality of coil winds and is the nominal ID of the coil. One or more coils 310 of the distal coil portion 208 may be formed from a radiopaque material (illustrated as solid coils 310 in distal coil portion 208). For example, the distal coil portion 208 may include a segment of stainless steel coil (e.g., 3 mm in length), followed by a segment of platinum coil (which is radiopaque and also 3 cm in length), followed by a segment of stainless steel coil (e.g., 3 mm in length), and so on and so forth.

A delivery wire 210 forms the first conductive path 242 and terminates at electrical contact 216 at one end and extends distally with respect to the distal coil portion 208 of the delivery wire assembly 200. The delivery wire 210 is coated with an insulative coating 218 such as polyimide except at the electrolytic detachment zone 220 and the proximal segment coupled to the electrical contact 216. The delivery wire 210 may have an OD of around 0.0125 inches. A centering coil 260 is affixed to the delivery wire 210 at a location within the distal coil portion 208. The centering coil 260 ensures that the delivery wire 210 is properly oriented within the delivery wire assembly 200. The centering coil 260 may be bonded directly to the delivery wire 210 using an adhesive 240 such as that described herein. To this end, an adhesive 240 is applied to secure the delivery wire 210 and centering coil 260 to the distal coil portion 208. The adhesive 240 may include EPO-TEK® 353ND-4 described in more detail above.

Still referring to FIG. 5, an outer sleeve 262 or jacket surrounds a portion of the proximal tubular portion 206 and a distal coil portion 208. The outer sleeve 262 covers the interface or joint formed between the proximal tubular portion 206 and the distal coil portion 208. The outer sleeve 262 may have a length of around 50 cm to around 54 cm. The outer sleeve 262 may be formed from a polyether block amide plastic material (e.g., PEBAX 7233 lamination). The outer sleeve 262 may include a lamination of PEBAX and HYDROLENE®. The outer diameter (OD) of the outer sleeve 262 may be less than 0.02 inches and advantageously less than 0.015 inches.

As seen in FIG. 5, a small segment 209 of the distal coil portion 208 is exposed distally beyond the outer sleeve 262. During use, this small segment 209 is exposed to conductive fluids and serves as the contact for the second conductive path 244 (e.g., return or ground path) of the circuit. This segment that projects distally may have a length greater than about 0.03 inches. The electrolytic detachment zone 220 is located about two millimeters (less in some embodiments) distal of the distal coil portion 208.

FIGS. 6A and 6B illustrate orthogonal, cross-sectional views of an occlusive coil 300 according to one embodiment. In this embodiment, a stretch resistant member 270 is secured at one end to the delivery wire adapter 230 and at the other end to the distal end 304 of the occlusive coil 300. The stretch resistant member 270 includes a distal cap or end 272 as best seen in FIG. 7B. The stretch resistant member 270 further includes a tether 274 which may take the form of a filament or the like. For example, the tether 274 may be formed from a polymeric material such as, for instance, suture filament material. During assembly of the occlusive coil 300, the stretch resistant member 270 exists initially as only a single tether 274 that extends from the distal cap 271. The free end of this tether 274 is fed through the aperture 250 located at the distal end 234 of the delivery wire adapter 230. The free end of the tether 274 is then pulled back toward the distal end 304 of the occlusive coil 300 where the same is bonded to the distal cap 272 to form the complete structure as illustrated in FIGS. 6A, 6B, and 7B. Heat bonding may be used to fuse or otherwise secure the free end of the tether 274 to the distal cap 272. Of course, other bonding techniques may also be used depending on the nature of the material used for the stretch resistant member 270. These include, for instance, welding, adhesive bonding, and the like. The use of a stretch resistant member 270 is entirely optional, however. Other embodiments may utilize an occlusive coil 300 that does not contain a stretch resistant member 270.

FIG. 7A illustrates a cross-sectional view of the occlusive coil 300 taken along the line A-A in FIG. 6A. The two tethers 274 of the stretch resistant member 270 are illustrated within the lumen 306 of the occlusive coil 300. FIG. 7B is an enlarged detailed view of detail B in FIG. 6B. The distal cap 272 of the stretch resistant member 270 is illustrated at the distal end 304 of the occlusive coil 300. FIG. 7C is an enlarged detailed view of detail C in FIG. 6A. The delivery wire adapter 230 is illustrated connecting the occlusive coil 300 and the delivery wire 210.

Figure 8:
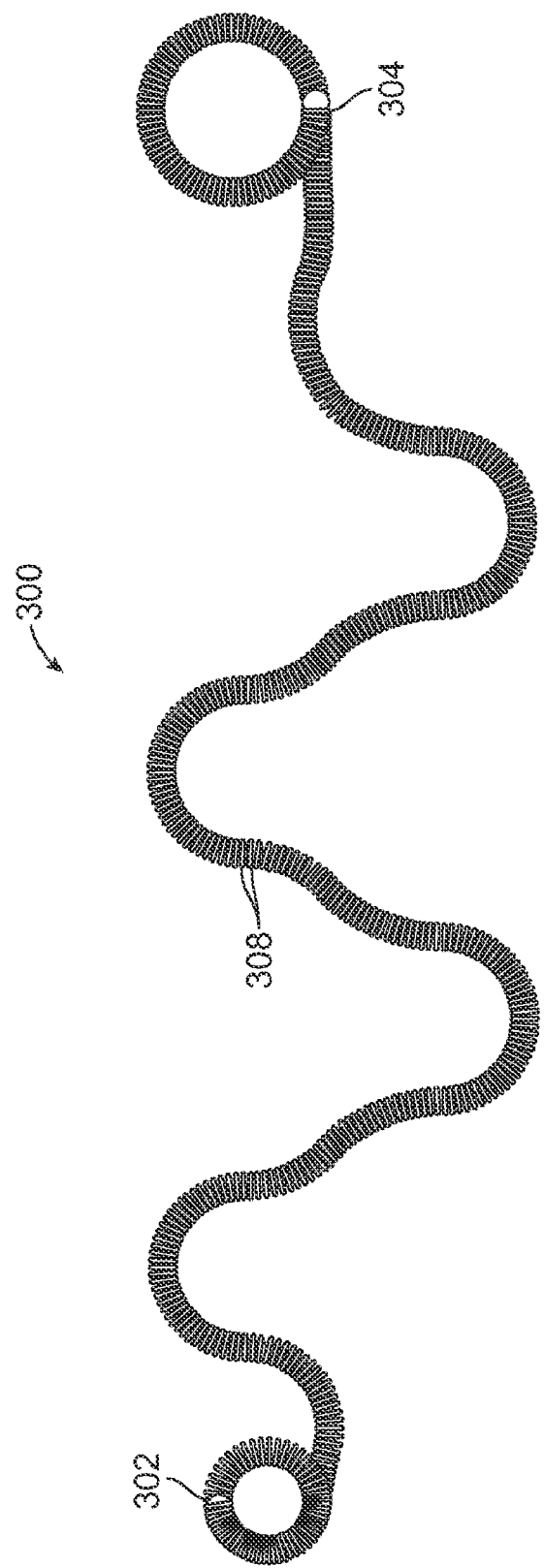
FIG. 8 illustrates an occlusive coil in a natural state mode illustrated one exemplary secondary configuration.

FIG. 8 illustrates one exemplary configuration of an occlusive coil 300 in a natural state. In the natural state, the occlusive coil 300 transforms from the straight configuration illustrated in, for instance, FIGS. 6A and 6B into a secondary shape. The secondary shaped may include both two and three dimensional shapes of a wide variety. FIG. 8 is just one example of a secondary shape of an occlusive coil 300 and other shapes and configurations are contemplated to fall within the scope of the invention. Also, the occlusive coil 300 may incorporate synthetic fibers over all or a portion of the occlusive coil 300 as is known in the art. These fibers may be attached directly to coil windings 308 or the fibers may be integrated into the occlusive coil 300 using a weave or braided configuration.

The delivery wire adapter 230 provides a number of advantages over previous embolic coil delivery systems. First, the delivery wire adapter 230 is a relatively short yet durable interface between the delivery wire 210 and the occlusive coil 300. There is no longer any long, stiff section in the delivery assembly that tends to cause kick-back. The delivery wire adapter 230 thus reduces or eliminates kick-back or recoil of the delivery wire assembly 200. The delivery wire adapter 230 also mitigates the risk of prolapsed of the occlusive coil 300 into the parent vessel. Further, the delivery wire adapter 230 can be used with different sized occlusive coils 300. A relatively simple adjustment of the size of the delivery wire adapter 230 may be made to accommodate occlusive coils 300 of many different sizes.

The small size of the delivery wire adapter 230 provides greater coil flexibility within the aneurysm and thus reduces delivery force necessary for full deployment of the occlusive coil 300. Finally, the delivery wire adapter 230 provides a strong junction between the delivery wire 210 and the occlusive coil 300. For example, a strong axial force (e.g., pulling the delivery wire assembly 200 and occlusive coil 300 in the proximal direction when the occlusive coil 300 is immobilized) will not cause a failure in the junction between the delivery wire 210 and the occlusive coil 300. Rather, the delivery wire adapter 230 is strong enough such that any failure mode would occur in the occlusive coil 300 for small coil wire diameters, or in the delivery wire/adapter junction for large coil wire diameters.

Another benefit of the system 10 described herein is that it utilizes a bipolar arrangement of the conductive paths 242, 244 in the actual delivery wire assembly 200. There is no longer any need to use a separate needle electrode that is inserted into the patient's groin area. Instead, the return or ground electrode is integrated into delivery wire assembly 200. This not only eliminates the need for the needle electrode but it results in more reproducible detachment times because there is no longer a large volume of tissue existing through which electrical current must pass.

Figure 9B:
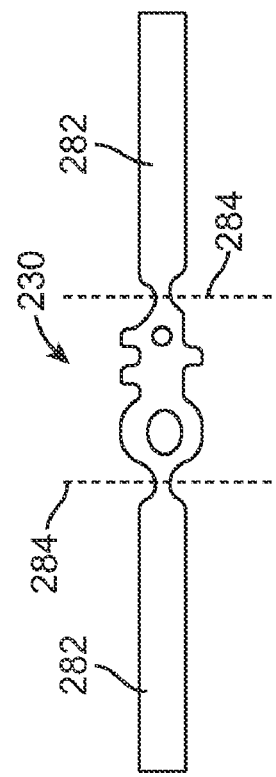
FIG. 9B illustrates a delivery wire adapter according to one embodiment.
Figure 9A:
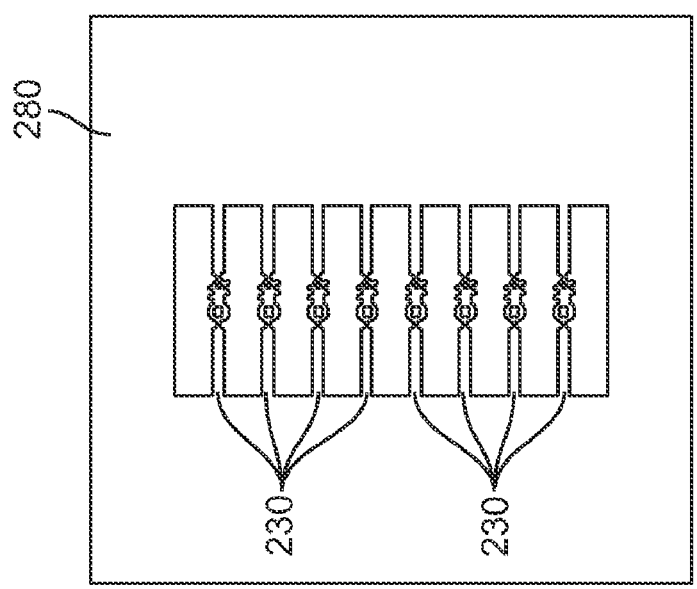
FIG. 9A illustrates a plurality of delivery wire adapters formed in a single substrate.

The delivery wire adapters 230 may be manufactured using a sheet or substrate 280 in which a plurality of delivery wire adapters are formed. FIG. 9A illustrates multiple delivery wire adapters 230 being patterned in a single substrate 280. The sheet or substrate 280 may include stainless steel such as hardened stainless steel 304 alloy. The thickness may vary depending on the desired thickness of the delivery wire adapter 230 but it generally is less than 0.003 inches. The delivery wire adapters 230 may be formed in the substrate 280 by photochemical etching. Of course, the various delivery wire adapters 230 may be formed in the substrate 280 through laser cutting, EDM machining, electroplating, or other process. As seen in FIGS. 9A and 9B, the delivery wire adapters 230 are initially formed with excess material 282 on either side of the delivery wire adapter 230. The excess material 282 is trimmed along cut-lines 284 to produce the final delivery wire adapters 230. Clippers or the like may be used to trim the excess material. Sharp edges formed in the delivery wire adapter 230 may be reduced by grit blasting, tumbling, or electro-polishing.

Figure 10:
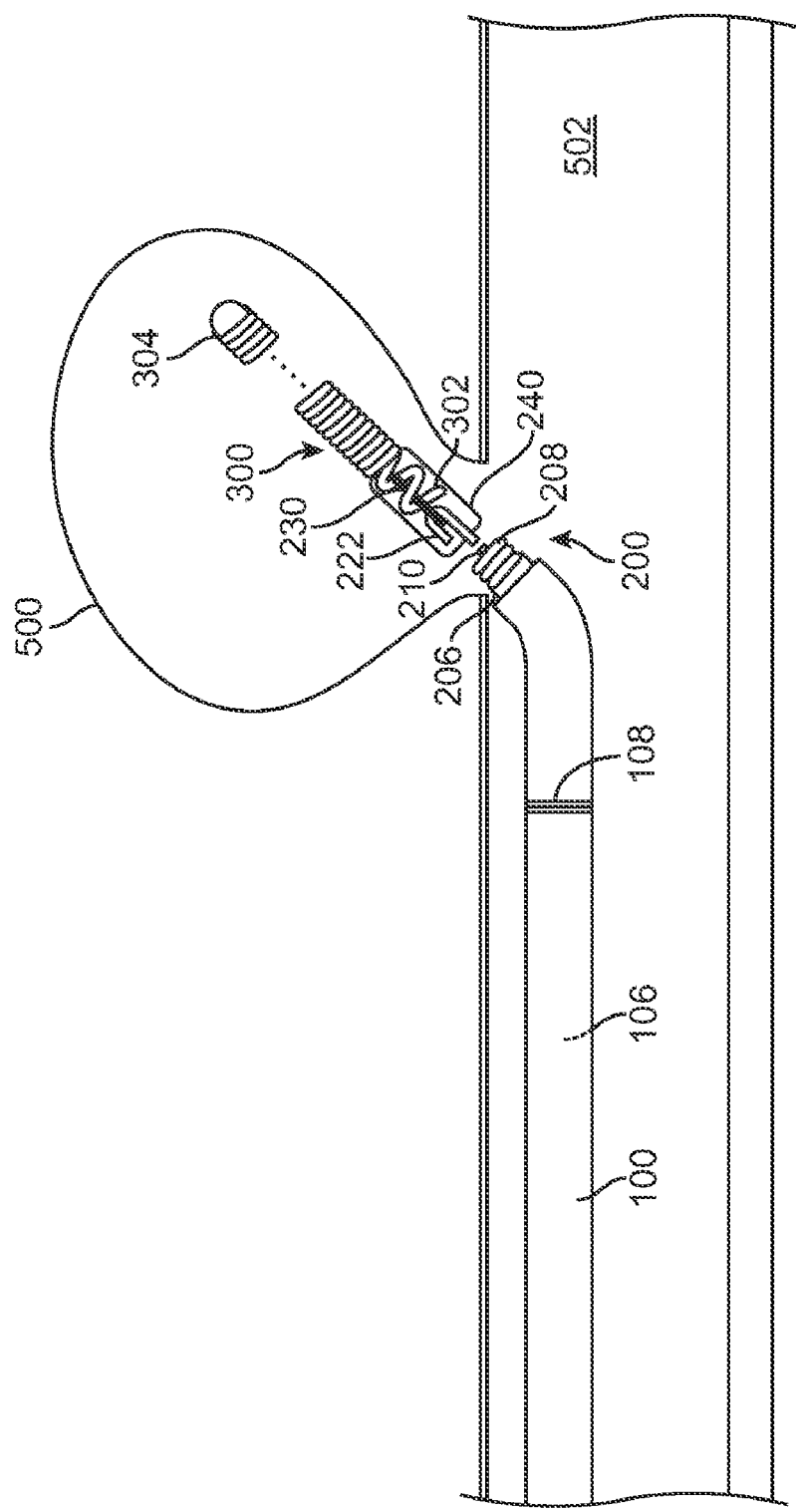
FIG. 10 illustrates detachment of an occlusive coil from a delivery wire assembly into an aneurysm according to one embodiment.

FIG. 10 illustrates an occlusive coil 300 being detached from the delivery wire 210 of the delivery wire assembly 200. In particular, the delivery wire assembly 200 is located within delivery catheter 100 that is positioned with a blood vessel 502. The delivery catheter 100 is typically advanced and placed into position under fluoroscopic guidance by the physician. Once positioned in place, the delivery wire assembly 200 can be advanced distally through the lumen 106 of the delivery catheter 100. Once the delivery wire assembly 200 has been advanced to place the occlusive coil 300 within the aneurysm 500, the physician can then trigger the power supply 400 by depressing trigger 408 to initiate current flow along the delivery wire 210. After several seconds, the electrolytic detachment zone 220, which is exposed to an electrically conductive solution, (either physiological or saline flush solution) dissolves away. The power supply 400 will detect breakage of the electrolytic detachment zone 220 and will stop delivery of electrical current. FIG. 10 illustrates separation of the occlusive coil 300 from the delivery wire assembly 200.

While embodiments of the present invention have been shown and described, various modifications may be made without departing from the scope of the present invention. The invention, therefore, should not be limited, except to the following claims, and their equivalents.

What is claimed is:

1. An occlusive coil delivery device, comprising:
an occlusive coil comprising a plurality of windings, the occlusive coil having a proximal end and a distal end, the proximal end of the occlusive coil comprising a plurality of open pitched windings;
a delivery wire assembly comprising a proximal tubular portion and a distal coil portion and lumen extending at least partially there through, the delivery wire assembly comprising a delivery wire forming a first conductive path extending at least partially within the lumen from a proximal end of the delivery wire assembly to a location distal of the distal coil portion, said delivery wire extending distal of the distal coil portion and comprising an electrolytic detachment zone, the delivery wire assembly further comprising a second conductive path formed by the proximal tubular portion and distal coil portion; and
a delivery wire adapter having a proximal end and a distal end, the distal end of the adapter comprising a plurality of fingers configured to interface between adjacent open pitched windings of the proximal end of the occlusive coil, the proximal end secured to a distal portion of the delivery wire.

2. The device of claim 1, wherein the proximal end of the delivery wire adapter comprises an aperture dimensioned to receive the distal portion of the delivery wire.

3. The device of claim 1, wherein the delivery wire is at least partially secured to the proximal end of the delivery wire adapter by an adhesive.

4. The device of claim 1, further comprising an outer sleeve encasing at least a portion of each of the proximal tubular portion and distal coil portion.

5. The device of claim 1, further comprising first and second electrical contacts disposed on a proximal region of the delivery wire assembly, the first and second electrical contacts electrically coupled to the first and second conductive paths, respectively, wherein the second electrical contact comprises an exposed region of the proximal tubular portion.

6. A system for delivering an occlusive coil, comprising:
a delivery catheter comprising a proximal end and a distal end and a lumen extending between the proximal and distal ends;
a delivery wire assembly comprising a proximal end and a distal end, the delivery wire assembly comprising a proximal tubular portion and a distal coil portion, the delivery wire assembly comprising a delivery wire forming a first conductive path extending from the proximal end of the delivery wire assembly to a location distal of the distal coil portion, said delivery wire extending distal of the distal coil portion and comprising an electrolytic detachment zone, the delivery wire assembly further comprising a second conductive path formed by the proximal tubular portion and distal coil portion;
an occlusive coil comprising a plurality of windings, the occlusive coil having a proximal end and a distal end, the proximal end of the occlusive coil comprising a plurality of open pitched windings;
a delivery wire adapter having a proximal end and a distal end, the distal end of the delivery wire adapter comprising a plurality of fingers configured to interface between adjacent open pitched windings of the proximal end of the occlusive coil, the proximal end of the delivery wire adapter configured for attachment to a distal portion of the delivery wire; and
a power supply configured to electrically connect to the first conductive path and the second conductive path.

7. The system of claim 6, wherein the distal coil portion comprises one or more integrated radiopaque coils.

8. The system of claim 6, wherein the first conductive path and the second conductive path terminate at respective electrical contacts disposed on the proximal end of the delivery wire assembly, the respective electrical contacts configured to engage corresponding electrical contacts disposed in the power supply, and wherein the electrical contact of the second conductive path comprises an exposed region of the proximal tubular portion.

9. The system of claim 6, wherein the distal coil portion is bonded to a distal end of the proximal tubular portion.

10. The system of claim 6, further comprising an outer sleeve disposed over the interface formed between the distal coil portion and the proximal tubular portion.

11. The system of claim 6, wherein the proximal end of the delivery wire adapter comprises an aperture dimensioned to receive a distal portion of the delivery wire.

12. The system of claim 6, wherein the delivery wire is at least partially secured to the proximal end of the delivery wire adapter with an adhesive.

* * * * *